United States Patent
Castiglioni et al.

(10) Patent No.: US 9,556,104 B2
(45) Date of Patent: Jan. 31, 2017

(54) PROCESS FOR HYDROGENATION OF ESTERS OF AROMATIC CARBOXYLIC ACIDS TO YIELD SATURATED HOMOLOGUES THEREOF

(71) Applicant: POLYNT S.P.A., Scanzorosciate (IT)

(72) Inventors: Gian Luca Castiglioni, Trescore Balneario (IT); Carlotta Cortelli, Zola Predosa (IT); Leonardo Poletti, Figline Valdarno (IT)

(73) Assignee: POLYNT S.P.A., Scanzorosciate (IT)

( * ) Notice: Subject to any disclaimer, the term of this patent is extended or adjusted under 35 U.S.C. 154(b) by 0 days.

(21) Appl. No.: 14/433,235

(22) PCT Filed: Oct. 2, 2013

(86) PCT No.: PCT/EP2013/070529
§ 371 (c)(1),
(2) Date: Apr. 2, 2015

(87) PCT Pub. No.: WO2014/053535
PCT Pub. Date: Apr. 10, 2014

(65) Prior Publication Data
US 2015/0246867 A1    Sep. 3, 2015

(30) Foreign Application Priority Data
Oct. 2, 2012 (IT) .............................. MI2012A1641

(51) Int. Cl.
| | | |
|---|---|---|
| *C08K 5/00* | (2006.01) | |
| *C07C 67/303* | (2006.01) | |
| *C08K 3/26* | (2006.01) | |
| *C07C 61/08* | (2006.01) | |
| *C08K 5/12* | (2006.01) | |
| *C08L 27/06* | (2006.01) | |

(52) U.S. Cl.
CPC ............ *C07C 67/303* (2013.01); *C07C 61/08* (2013.01); *C08K 3/26* (2013.01); *C08K 5/12* (2013.01); *C08L 27/06* (2013.01); *C07C 2101/14* (2013.01)

(58) Field of Classification Search
CPC .... C07C 67/303; C07C 61/08; C07C 2101/14; C08K 5/12; C08L 27/06
USPC ........................................................ 524/285
See application file for complete search history.

(56) References Cited

U.S. PATENT DOCUMENTS

| | | |
|---|---|---|
| 2,070,770 A | 2/1937 | Amend |
| 3,027,398 A | 3/1962 | Foohey |
| 3,334,149 A | 8/1967 | Akin et al. |
| 4,327,780 A | 5/1982 | Lehmann |
| 5,286,898 A | 2/1994 | Gustafson et al. |
| 6,284,917 B1 * | 9/2001 | Brunner .................. C07C 51/36 560/127 |
| 7,208,545 B1 | 4/2007 | Brunner et al. |
| 2005/0101800 A1 | 5/2005 | Buschken et al. |

FOREIGN PATENT DOCUMENTS

| | | |
|---|---|---|
| DE | 1154096 | 9/1963 |
| DE | 2132547 | 1/1973 |
| DE | 2823165 | 11/1979 |
| EP | 0005737 A1 | 12/1979 |
| GB | 286201 | 10/1929 |
| WO | WO 94/29261 A1 | 12/1994 |
| WO | WO 99/32427 A1 | 7/1999 |
| WO | WO 2004/046078 A1 | 6/2004 |

OTHER PUBLICATIONS

Wilkes C.E. et al., PVC Handbook Chapter 5.4, "Types of Plasticizers",, ISBN 3-446-22714-8 (2005) (25 pages total).
International Search Report dated Apr. 15, 2014 issued in PCT/EP2013/070529.

* cited by examiner

*Primary Examiner* — Hui Chin
(74) *Attorney, Agent, or Firm* — Scully, Scott, Murphy & Presser, P.C.

(57) ABSTRACT

A process for the hydrogenation of substituted aromatic compounds, with particular reference to esters of aromatic carboxylic acids, for example of aromatic esters used commonly as plasticizers in polymers having wide commercial application (see, in particular, esters of phthalic acid and trimellitic acid).

23 Claims, No Drawings

PROCESS FOR HYDROGENATION OF ESTERS OF AROMATIC CARBOXYLIC ACIDS TO YIELD SATURATED HOMOLOGUES THEREOF

FIELD OF THE INVENTION

The present invention relates to a new process for the hydrogenation of substituted aromatic compounds, with particular reference to esters of aromatic carboxylic acids, for example of aromatic esters commonly used as plasticizers in polymers having wide commercial application (see in particular diesters of phthalic acid and triesters of 1,2,4-benzene tricarboxylic acid), and the invention also relates to new saturated products obtainable/obtained from the hydrogenation of respective aromatic precursors, as well as to new uses of the saturated products obtainable/obtained from hydrogenation in the frame of the plasticizing of polymers for particular purposes.

The present invention also relates to new mixtures between polymers and said new saturated products.

BACKGROUND ART

Several processes for the hydrogenation of esters of aromatic carboxylic acids (where the expression "carboxylic acids" is understood to reference both monocarboxylic acids and polycarboxylic acids) to yield the corresponding saturated homologues (i.e., where applicable, mixtures thereof of isomers produced by hydrogenation) have been known now for almost 100 years in the background art. Many of such processes are based on heterogeneous catalysis with active metals and are performed in the liquid or gaseous phase with or without the use of reaction solvents/diluents, exposing the initial aromatic ester and a hydrogen source (almost always a hydrogenating gas, which often but not necessarily is constituted by pure hydrogen) to contact with the active metal catalyst, conducting the consequent exothermic hydrogenation reaction in semi-continuous or continuous conditions.

A common factor of such known processes for hydrogenation of aromatic acid esters is the use of rather high hydrogenating gas pressures during the reaction, especially if the reaction is performed in the liquid phase, and this occurs in most processes used on an industrial scale, in particular if related to scarcely volatile aromatic carboxylic acid esters.

For example, GB 286,201 discloses a reaction of aromatic carboxylic acid esters conducted at temperatures comprised between 120° and 150° C. and at pressures between 25 and 40 bars in the presence of nickel catalysts.

U.S. Pat. No. 2,070,770 notes that the reactions according to GB 286,201 are considered slow and not quantitative, in addition to being limited to the corresponding ethyl esters, and therefore teaches a process for the hydrogenation of dialkyl esters of phthalic acid with alcohols comprising at least 8 carbon atoms, performed at 160-260° C. and at 750 psi (51.7 bar)-5000 psi (344.7 bar).

U.S. Pat. No. 3,027,398 relates instead to the catalytic hydrogenation of dimethyl terephthalate performed at 110-140° C. at 500 psi (34.5 bar)-1500 psi (103.4 bar), in which the initial dimethyl terephthalate is dissolved in dimethyl 1,4 cyclohexane dicarboxylate (which is the saturated product) as reaction solvent.

DE 1 154 096 discloses the hydrogenation of C1-C5 alkyl terephthalate at temperatures comprised between 150° C. and 250° C. and at hydrogen pressures comprised between 20 and 300 atmospheres, with the addition of 10-25% by weight (relative to the terephthalate) of alkyl ester of p-toluic acid and/or ester of 4-methyl cyclohexanecarboxylic acid in the presence of nickel.

U.S. Pat. No. 3,334,149 teaches the hydrogenation of molten alkyl terephthalate at pressures comprised between 50 and 500 atmospheres and temperatures comprised between 100° C. and 400° C., preferably 150-275° C., on a fixed bed palladium catalyst.

DE 2 132 547 relates instead to the hydrogenation of aromatic compounds (including benzoic acid esters or phthalic acid esters and isomers) at temperatures comprised between 30° and 250° C. and at pressures in excess of 50 bars with ruthenium catalysts.

DE 28 23 165 teaches the catalytic hydrogenation of esters of aromatic carboxylic acids on a fixed bed of catalyst of nickel, ruthenium, rhodium or palladium, at temperatures between 70° C. and 250° C. and at pressures between 30 and 200 bars in the liquid phase or at the same temperature and at pressures between 1 and 10 bar in the gaseous phase.

WO 99/32427 discloses the hydrogenation of esters and anhydrides of benzene polycarboxylic acids at temperatures comprised between 50° C. and 250° C. at pressures in excess of 10 bar, comprised preferably between 20 and 300 bar, using three different types of catalyst. The reactions exemplified in WO 99/32427 are performed in the liquid phase and at pressures of 100 or 200 bar.

US52869898 concerns a process for the preparation of dimethyl cyclohexane carboxylate by hydrogenation of dimethyl benzenedicarboxylate. The preferred temperature is in the range of 140-220° C. and the preferred pressure range is 50-170 bars absolute. The catalyst employed comprises palladium and a second Group VIII metal. According to the optimum conditions detailed, the reactions are carried out in continuous modus at a pressure of 125.1 bars.

US2005/101800 concerns the preparation of cycloaliphatic polycarboxylic esters by hydrogenating a partial ester of the corresponding aromatic carboxylic acid or of the corresponding aromatic polycarboxylic anhydride, and, thereafter, reacting the resultant cycloaliphatic partial ester with an alcohol to give the sought full ester.

WO 94/29261 reports on the low yields obtained applying the processes described in older patent literature when the hydrogen pressure employed for the hydrogenation of dimethyl terephtalate is lower than about 135 bars absolute. Before this background, WO 94/29261 proposes a continuous process for the manufacture of a cyclohexanedicarboxylate.

WO 2004/046078 concerns hydrogenation of benzenepolycarboxylic acid derivatives to give corresponding cyclohexylderivatives. The most preferred pressures applied exceed 100 or 130 bar, with a maximum of about 300 bar. Preferably, the process is carried out continuously and in the presence of a solvent.

US 57208545 concerns the hydrogenation of novel substrates substrates which are different from diesters of phthalic acid and from triesters of 1,2,4-benzene tricarboxylic acid It is thus evident that the pressures of hydrogenating gas commonly used in the background art to saturate polycarboxylic acid esters in the liquid phase exceed on average 20-30 bar, often exceed even at least 50 bar, and therefore require an adequate mechanical sizing of the equipment used, which must withstand such pressures, and must be protected adequately against the risk of hydrogen embrittlement.

On this background, in the background art there is the need to provide new processes for the liquid phase hydrogenation of aromatic carboxylic acid esters that do not entail these disadvantages and therefore provide improved or alternative access to the respective hydrogenated products.

This occurs because in recent times cyclohexanecarboxylic esters, particularly esters of hexahydrophthalic acid with C1-C16 alkanols or mixtures thereof, have generated considerable commercial interest as products that can be used potentially to replace at least partially certain phthalic plasticizers that are traditionally used widely in plastic materials but were subjected to restrictions by the European Union in 2007, for example as regards use in toys, in articles for babies and in articles intended for contact with food. Potential risks arising from phthalic plasticizers that are widely used have also been hypothesized for medical articles and devices (blood bags, enteral nutrition kits, etc.). Several phthalic plasticizers, such as for example di-2-ethylhexyl phthalate (identified below as "DEHP" and also sometimes termed less specifically in the literature as DOP—di-ocytl phthalate), di-isobutyl phthalate (DIBP), and n-butyl phthalate (DBP), are therefore currently included in the so-called "SVHC List" (Substances of Very High Concern) prepared by the European Chemicals Agency (ECHA). For this reason, the assessment of replacement of these substances with other alternative ones that do not have toxicological problems is already in progress. Consequently, the identification of molecules that are alternative to those included in the SVHC list is of considerable interest for modern chemical industry.

Necessarily, it is essential that the identified molecules have technical characteristics that are comparable to the extremely advantageous and particular ones of traditional phthalic plasticizers. As regards for example the processing behavior characteristics (or "workability") of esters of cyclohexanedicarboxylic acids, the "PVC Handbook" by Charles E. Wilkes et al. (ISBN 3-446-22714-8), in its 2005 edition, predicted on page 185 that for example di-isononyl cyclohexane 1,2 dicarboxylate (HDINP), a hydrogenated product that is "homologous" to traditional di-isononyl phthalate (DINP), recently introduced on the market for some of the most sensitive plastic material applications in the pediatric and medical field, will have a performance that is substantially similar to the respective phthalate, except for the expectation of a reduced dissolving power of the polymer where it comprises PVC, which can be deduced from the loss of the aromaticity of the ring in di-isononyl cyclohexane 1,2 dicarboxylate.

However, it was found subsequently that the differences between phthalate and direct hexahydrophthalic homologue can be even considerable in practice, especially as regards the processing behavior of the mixtures between plasticizer and polymer. The former is of interest since the processing behavior, especially the incorporation time of the plasticizers into the most employed types of polymer preparations (such as e.g. dry-blend or plastisol) is a critical parameter for the efficiency (either in terms of energy consumption or output) of the overall polymer working process aiming at the provision of objects made from plasticized polymer.

Thus, for example, a study entitled "Plastisol ReFlex™ 100 Evaluation" published in May 2011 by the Pasadena Plasticizer Application Lab (PPL) on the Internet for PolyOne at the address http://www.polyone.com/en-us/docs/Documents/Plastisol_reFlex %28TM %29_100_Evaluation.pdf teaches that in order to obtain processing behavior characteristics that can be compared to the use of pure DINP as plasticizer (in particular in order to obtain the same processing temperature of the respective PVC plastisols) it is necessary to use mixtures between 65% by weight of di-isononyl cyclohexane 1,2 dicarboxylate (HDINP) and 35% by weight of epoxidized fatty acid monoester, since the melting point of the plastisols prepared only with di-isononyl cyclohexane 1,2 dicarboxylate (HDINP) exceeds by as much as 15° the fusion temperature of conventional plastisols, i.e., those that contain the same quantity of pure DINP.

Therefore, the recent study by PPAL confirms that the processing behavior of di-isononyl cyclohexane 1,2 dicarboxylate (HDINP) in PVC is actually reduced with respect to DINP, a fact which leads subsequently, for example, to a reduced production rate and/or to a higher energy expenditure in plastisol processing applications.

Besides the comparison with its direct "homologue" DINP, the industrial applicability of di-isononyl cyclohexane 1,2 dicarboxylate (HDINP) on a more general scale, potentially almost a universal one, is to be evaluated also—in view of its compatibility with an already broad and rapidly growing range of toxicologically safer products—with respect to DEHP, which is instead the current plasticizer of reference in very wide generic use. According to the above cited PVC Handbook (see in particular Chapter 5.4, "Types of plasticizers", specifically the discussion of phthalates on page 177 and table 5.2 on pages 179-180), di-2-ethylhexyl phthalate (DEHP) is used historically as a common reference standard to evaluate the performance of all other plasticizers, both phthalic and otherwise, and is used further as a standard to conceive theoretically mixtures of plasticizers for specific applications.

As explained below in the present application, the inventors of the present invention have been able to confirm, as part of their studies, that di-isononyl cyclohexane 1,2 dicarboxylate (HDINP) is inferior, as regards some particular characteristics related to processing, specifically to its incorporation time in the polymer or in the polymeric mixture, such as the dry blend time or the gel time or fusion time, both to DOP (or DEHP), i.e., the current plasticizer of reference, and to DINP (its direct aromatic homologue), especially as regards applications for PVC.

It is therefore evident that the hydrogenation of the aromatic system in certain aromatic plasticizers, more concretely the transition from DINP to HDINP, can compromise the processing behavior of the resulting polymer/plasticizer mixture; in particular, hydrogenation can compromise the processing behavior in dry blends and in plastisols of PVC, and consequently can lower the production rate in PVC applications. This loss of performance in PVC can constitute, at least for less sensitive generic applications (i.e., of the general-purpose type, as classified by the PVC Handbook), especially if subject to large-scale production, an obstacle to a wider establishment of di-isononyl cyclohexane 1,2 dicarboxylate (HDINP) or similar products on the market.

As regards instead special or very special applications (so-called "specialty plasticizers" (SP), according to the PVC Handbook), it should be noted that in some fields of technology, for example where plasticizers with extremely low diffusivity are required (see SP-LD plasticizers, again as in the PVC Handbook), plasticizers are already in use which are free or substantially free from phthalates and therefore are already compatible with 2007 UE standards et seq.

This is the case, for example, of trimellitates, which are triesters of 1,2,4-benzene tricarboxylic acid (comprising, for example tri-2-ethylhexyl trimellitate or TOTM, tri-isooctyl trimellitate or TIOTM, tri-n-octyl trimellitate or TM8, triisononyl trimellitate or TINTM, tributyl trimellitate or TM4, trimellitate of C7-C9 linear alkanols or TM7-9, trimellitate of C8-C10 linear alkanols or TM8-10 and others) and are distinguished—with respect to the reference DEHP—by extremely reduced volatility and higher resistance to extraction, exhibiting at the same time excellent electrical properties.

These characteristics qualify trimellitates traditionally for use in insulators, for example for electrical cables, especially if rated for high temperatures, for use in leathers and in synthetic coverings for car interiors—and more generally for all applications in which one wishes to minimize the release of plasticizer from the mixture with the polymer, especially if exposed to heat sources (see PVC Handbook, page 330).

However, the processing behavior of plasticizers of the trimellitate class is reduced with respect to DEHP of common reference, especially if the trimellitates are used in a mixture with PVC.

Therefore, it would be desirable to identify, preferably in the field of special applications, particularly in the field of SP-LD plasticizers to which trimellitates belong, alternative plasticizers that are still free from phthalates but improve the processing behavior of the polymer/plasticizer mixtures that contain them, in particular of PVC-based plastic mixtures. This would make available new mixtures between SP-LD plasticizer and polymer, in particular new mixtures comprising plasticizer and PVC, free from phthalates but at the same time characterized by better processing behavior.

Moreover, as seen above, although the study of hydrogenation of aromatic esters is in progress since the 1920s and despite the many possibilities developed for plasticizing synthetic polymers that appeared after the Second World War, in the background art there is still considerable interest in identifying new advantageous technical applications of plasticizers (or mixtures thereof) with reduced toxicity, preferably free from phthalates, applications that entail performances comparable or improved with respect to traditional plasticizers, in providing new processes for the hydrogenation of esters of aromatic carboxylic acids, as an alternative or as an improvement to known hydrogenation processes, in order to facilitate the provision of plasticizers with reduced toxicity and thus have available additional sources of said plasticizers that can be used for the above-cited new applications, and in providing new plasticized polymeric mixtures comprising polymers and plasticizers with reduced toxicity, particularly free from phthalates, that have improved applicability.

The aim of the present invention is therefore to solve the problems observed in the background art.

SUMMARY OF THE INVENTION

According to a first embodiment, the present invention relates to a process for the semi-continuous catalytic liquid phase hydrogenation of esters of aromatic carboxylic diacids and triacids, preferably selected from diesters of phthalic acid and triesters of 1,2,4-benzene tricarboxylic acid, wherein the esters, loaded in a reactor without adding diluent/solvent, are hydrogenated at an internal temperature of the reactor comprised in the range from 100° C. to 200° C., preferably from 120° C. to 190° C., more preferably from 130° C. to 180° C., even more preferably from 140° C. to 170° C., by continuously feeding a hydrogenation gas into the reactor, controlling the hydrogenation gas pressure inside the reactor to values lower than 18 bar gauge (barg), preferably equal to or lower than 15 barg, more preferably comprised in the range from 9 to 15 barg and in the presence of 0.1-3% by weight, preferably 0.3-1.5% by weight, relative to the quantity of esters of aromatic carboxylic acids loaded into the reactor, of a supported catalyst comprising between 0.1 and 10% by weight, relative to the total weight of the catalyst, of an active metal of the group consisting of ruthenium, rhodium, palladium, osmium, iridium, platinum, gold or mixtures thereof, and optionally of at least one additional metal selected from groups I-III of the periodic system, also present at most as 10% by weight, relative to the total quantity of catalyst, and present in a quantity that does not exceed that of the active metal. In said process, the catalyst is preferably used in suspension. Said process uses preferably esters of aromatic carboxylic diacids selected from diesters of phthalic acid with non-cyclic monofunctional alkanols comprising 1 to 16 carbon atoms or mixtures thereof. As a preferred alternative, said method uses more preferably esters of aromatic carboxylic triacids selected from triesters of 1,2,4-benzene tricarboxylic acid with non-cyclic monofunctional alkanols comprising 1 to 16 carbon atoms or mixtures thereof.

According to a second embodiment, the present invention relates to new polymeric compositions comprising a polymer, preferably PVC (or a mixture between PVC and another polymer) and a plasticizer selected from the group that consists of triesters of 1,2,4-cyclohexanecarboxylic acid with non-cyclic monofunctional alkanols comprising 1 to 16 carbon atoms, preferably 7 to 11, more preferably 8 to 10 carbon atoms or mixtures thereof. For example, the present invention relates to new polymeric compositions comprising a polymer, preferably PVC or a mixture of PVC with another polymer, and at least one plasticizer selected from the group that consists of 1,2,4-tri-2-ethylhexyl cyclohexane carboxylate (HTOTM), 1,2,4-tri-nC7-nC9 cyclohexane carboxylate (HTM7-9), 1,2,4-tri-nC8 cyclohexane carboxylate (HTM8), 1,2,4-tri-nC8-nC10 cyclohexane carboxylate (HTM8-10), 1,2,4-tri-nC9-nC11 cyclohexane carboxylate (HTM9-11), 1,2,4-tri-nC9-iC9-nC11 cyclohexane carboxylate (HTM99-11) and 1,2,4-tri-iC9 cyclohexane carboxylate (HTINTM).

According to a third embodiment, the present invention relates to the use of 1,2,4-trialkyl cyclohexane carboxylates or mixtures thereof, preferably the use of triesters of 1,2,4-trialkyl cyclohexanecarboxylic acid with non-cyclic monofunctional alkanols comprising 1 to 16 carbon atoms or mixtures thereof as plasticizers for polymers in order to reduce the incorporation times of said triesters of 1,2,4-trialkyl cyclohexanecarboxylic acid in a polymer with respect to the incorporation of the respective triesters of trimellitic acid or mixtures thereof as polymer plasticizers. Preferably, the 1,2,4-trialkyl cyclohexane carboxylates or mixtures thereof used by the invention are constituted by triesters of 1,2,4-cyclohexanecarboxylic acid with non-cyclic monofunctional alkanols comprising 1 to 16 carbon atoms, more preferably 7 to 11, even more preferably 8 to 10 carbon atoms. The incorporation times comprise for example the dry blend time of so-called dry blend preparations (polymer granules that have absorbed the plasticizer) or the gelification time or fusion time of dry blend preparations and of plastisol preparations (viscous pastes of polymer and plasticizer). In the field of use according to the third embodiment, preference is given for example to 1,2,4-tri-C1 cyclohexane carboxylate (HTM1), 1,2,4-tri-C2 cyclohexane carboxylate (HTM2), 1,2,4-tri-iC3 cyclohexane carboxylate (HTMI3), 1,2,4-tri-nC4 cyclohexane carboxylate (HTM4), 1,2,4-tri-nC4 cyclohexane carboxylate (HTMI4), 1,2,4-tri-2-ethylhexyl cyclohexane carboxylate (HTOTM), 1,2,4-tri-nC7-nC9 cyclohexane carboxylate (HTM7-9), 1,2,4-tri-nC8 cyclohexane carboxylate (HTM8), 1,2,4-tri-iC8 cyclohexane carboxylate (HTIOTM), 1,2,4-tri-nC8-nC10 cyclohexane carboxylate (HTM8-10), 1,2,4-tri-nC9 cyclohexane carboxylate (HTM9), 1,2,4-tri-nC9-nC11 cyclohexane carboxylate (HTM9-11), 1,2,4-tri-nC9-nC11 cyclohexane carboxylate (HTM11), 1,2,4-tri-nC9-iC9-nC11 cyclohexane carboxylate (HTM99-11), 1,2,4-tri-iC9 cyclohexane carboxylate (HTINTM) and 1,2,4-tri-nC12 cyclohexane carboxylate (HTM12).

Among the above, particular preference is given to 1,2,4-tri-2-ethylhexyl cyclohexane carboxylate (HTOTM), 1,2,4-tri-nC7-nC9 cyclohexane carboxylate (HTM7-9), 1,2,4-tri-nC8 cyclohexane carboxylate (HTM8), 1,2,4-tri-nC8-nC10 cyclohexane carboxylate (HTM8-10), 1,2,4-tri-nC9-nC11 cyclohexane carboxylate (HTM9-11), 1,2,4-tri-nC9-iC9-nC11 cyclohexane carboxylate (HTM99-11) and 1,2,4-tri-iC9 cyclohexane carboxylate (HTINTM).

Still within the scope of the use according to the third embodiment of the present invention, 1,2,4-tri-2-ethylhexyl cyclohexane carboxylate (HTOTM) is the most preferred.

Preferably, the previous use entails the reduction of the dry blend time with respect to the use of the respective triesters of trimellitic acid or mixtures thereof as plasticizers of a polymer, preferably of PVC or of a mixture thereof with another polymer. Preferably, this reduction of the dry blend time, measured in the temperature range from 83° C. to 103° C. with 50 or 60 parts of plasticizer on 100 parts of PVC, amounts to at least 3%, more preferably at least 5%, and even more preferably at least 7%. Preferably, said reductions in dry blend time are established by means of torque measurements with a Brabender plastograph (P600 cell).

As an alternative, the previous use entails preferably the reduction of gelification time or fusion time with respect to the use of the respective triesters of trimellitic acid or mixtures thereof as plasticizers of a polymer, preferably of PVC or of a mixture thereof with another polymer. Preferably, the previous use entails the reduction of the gelification time, measured in the temperature range from 88° C. to 108° C. with 50 parts of plasticizer on 100 parts of PVC, by at least 7%, more preferably at least 15%, even more preferably at least 30% with respect to the use of the respective triesters of trimellitic acid or mixtures thereof.

Preferably, the above cited gelification time reductions are established by means of torque measurements with a Brabender plastograph (W-50 cell).

As an alternative, the previous use entails preferably the reduction of the solution temperature (DIN 53408) with respect to the use of the respective triesters of trimellitic acid or mixtures thereof as plasticizer of a polymer, preferably of PVC or of a mixture thereof with another polymer.

In the second and third embodiments of the invention as described here, the polymer subjected to plasticizing is preferably PVC (or mixtures thereof), particularly S-PVC (or mixtures thereof).

DETAILED DESCRIPTION OF THE INVENTION

A first aspect of the present invention relates to a new process for the hydrogenation of esters of aromatic carboxylic acids, which can be performed with excellent yields and in shorter times in plants designed for medium-low pressures, with a consequent saving in investment costs. More particularly, the first aspect of the present invention relates to a process for the semi-continuous liquid phase catalytic hydrogenation of esters of aromatic carboxylic diacids and triacids, preferably selected from phthalic acid diesters and triesters of 1,2,4-benzene tricarboxylic acid, in which the esters, loaded into a reactor without the addition of diluent/solvent, are hydrogenated at an internal temperature of the reactor comprised in the range between 100° C. and 200° C., preferably 120° C. to 190° C., more preferably 130° C. to 180° C., even more preferably 140° C. to 170° C., by continuous feeding of a hydrogenation gas into the reactor, controlling the pressure of the hydrogenation gas inside the reactor to values of lower than 18 barg, preferably equal to or lower than 15 barg, more preferably in a range from 9 to 15 barg and in the presence of 0.1-3% by weight, preferably 0.3-1.5% by weight, relative to the quantity of esters of aromatic carboxylic acids loaded into the reactor, of a supported catalyst comprising 0.1 to 10% by weight, relative to the total weight of the catalyst, of an active metal of the group consisting of ruthenium, rhodium, palladium, osmium, iridium, platinum, gold or mixtures thereof, and optionally at least one additional metal selected from groups I-III of the periodic system, also present at most as 10% by weight, relative to the total quantity of catalyst, and present in a quantity that does not exceed that of the active metal.

As mentioned, the process of hydrogenation of aromatic esters in general as known in the background art is often performed in semi-continuous or continuous reactors, with relatively high or very high hydrogen pressures (50 to 200 bars in the preferred modes) and temperatures that vary depending on the substrate and on the process. Hydrogenation can occur in bulk or in the presence of a solvent/diluent. The catalysts are on average based on metals of group VIII, almost always supported on several supports with different surface areas and different porosities. For example, the hydrogenation of tricarboxylic esters is described in WO 99/32427, and one of the examples of this patent shows the results of hydrogenation of tri-2-ethylhexyl trimellitate (TOTM) to tri-2-ethylhexyl 1,2,4-cyclohexane tricarboxylate (HTOTM). In another example, reference is made to 1,2,4-tri (linear) C6-C8 trimellitate (NHOTM or TM6-8). In both cases, a catalyst based on 0.05% Ru on Al2O3 was used. For further details, refer to the summary table of the two examples of WO 99/32427 shown below.

| Example No. | Ru/Al$_2$O$_3$ g | Substrate type | g | Solvent type | T ° C. | P bar | Duration h | Conv. % | Yield % |
|---|---|---|---|---|---|---|---|---|---|
| 12 | 53 | TOTM | 800 | NO | 100 | 200 | 20 | 95 | 94 |
| 13 | 10 | TM6-8 | 150 | NO | 120 | 200 | 11 | 100 | 99.2 |

The process according to the present invention is performed in a semi-continuous mode. The entire (aromatic) substrate to be hydrogenated is loaded into the reactor together with the catalyst, but without the use of solvents. The catalyst is of the supported type and comprises 0.1 to 10% by weight, relative to the total weight of the catalyst, of an active metal of the group consisting of ruthenium, rhodium, palladium, osmium, iridium, platinum and mixtures thereof. Optionally, in the catalyst there can be at least one additional metal, present at most as 10% by weight, with respect to the total quantity of catalyst and in a quantity that does not exceed that of the active metal. The catalyst is added to the reactor in a quantity of 0.1-3% by weight, preferably 0.3-1.5% by weight, relative to the quantity of aromatic substrate loaded into the reactor. One then proceeds optionally with the inerting of the reactor with an inert gas, for example nitrogen, and then the internal temperature is increased to the reaction start T (at least 100° C., preferably 120° C., more preferably 130° C., even more preferably approximately 140° C.). In some particularly preferred cases, the internal temperature set for the commencement of the reaction is 150° C. At this point the continuous feeding of hydrogen begins, with consequent consumption of the hydrogen by the aromatic substrate with saturation of the ring. As the reaction kinetics slows down, the unreacted hydrogen increases the pressure inside the reactor until a value set initially on the pressure reduction unit on the hydrogen supply line is reached (preferably at values lower than 18 barg, preferably equal to or lower than 15 barg, more preferably in the range between 7 and 15, preferably between 9 and 15 barg). Once the P set on the reduction unit has been reached, as a function of the degree of conversion reached, the conversion is completed optionally by increasing the temperature gradually to maximum Ts of 150-200° C., preferably 150-170° C., more preferably 160-170° C. In other words, the feeding of hydrogenation gas is controlled during the hydrogenation reaction so as to increase the pressure inside the reactor with increasing conversion, and the feeding of hydrogenation gas continues until the internal pressure of the reactor reaches a value that is preferably comprised in a range between 9 and 15 barg at an internal temperature comprised preferably in the range between 150 and 170° C. The reaction is ended when no consumption of hydrogen occurs for a time interval that can vary between 0.25 and 1 h, after which the reaction mixture is subjected to separation of the hydrogenated esters that have formed. Preferably, agitation is provided inside the reactor and can be supplied by an adapted agitator that facilitates the recycling of the hydrogen inside the reactor. At the end of the reaction, the catalyst can be recycled and reused as it is, so as to reduce its specific consumption. It is possible (optional), furthermore, to add to the recycled catalyst a small amount of fresh catalyst in order to improve its activity and selectivity.

Preferably, the process for catalytic hydrogenation according to the present invention uses as initial substrate esters of aromatic carboxylic diacids selected from phthalic acid diesters with non-cyclic monofunctional alkanols comprising 1 to 16 carbon atoms or mixtures thereof.

More preferably, the process for catalytic hydrogenation according to the present invention uses esters of aromatic carboxylic triacids selected from triesters of 1,2,4-benzene tricarboxylic acid with non-cyclic monofunctional alkanols comprising 1 to 16 atoms of carbon or mixtures thereof.

In both of the above-cited cases—of which the second is the preferred one—the non-cyclic monofunctional alkanol is selected preferably from the group that consists of methanol, ethanol, n-butanol, sec-butanol, iso-butanol, tert-butanol, n-hexanol, 2-ethyl hexanol, n-heptanol, n-octanol, n-nonanol, i-nonanol, n-decanol, i-decanol, n-undecanol and n-dodecanol or mixtures thereof, preferably from the group consisting of 2-ethyl hexanol, n-heptanol, n-octanol, n-nonanol, i-nonanol, n-decanol, i-decanol, n-undecanol and n-dodecanol, more preferably 2-ethyl hexanol.

As an alternative to the above-cited specified alkanols, the non-cyclic monofunctional alkanol comprises 7-12 carbon atoms, preferably 8-11, even more preferably 8-10 carbon atoms.

Adequate supports for the above-cited catalysts are all the ones usually used and described for hydrogenation reactions and constituted therefore for example by coal, silicon carbide, aluminum oxide, silicon dioxide, titanium dioxide, zirconium dioxide, magnesium oxide, zinc oxide or mixtures thereof. Particular preference is given to catalysts that comprise an active metal selected from Ru, Rh or Pd or mixtures thereof on a support of coal or alumina, as widely commercially available.

More particularly, it is possible to use for example Pd on alumina or coal and/or Ru on coal and/or Rh on coal. Preferably, the active metal is present between 1.5 and 7.0% by weight, relative to the total weight of the catalyst. Preferably, the surface area (BET method) is comprised between 100 and 350 $m^2/g$, the volume of the pores is between 0.3 and 0.9 cc/g and the average pore size is between 20 and 250 Å.

It has been found, in any case, that the process according to the invention does not depend substantially on the exact type of hydrogenation catalyst used, so long as the catalyst matches the specifications given here. The process according to the invention in fact allows to obtain a conversion of 98% or more (preferably 99% or more) with molar yields of 97% or more (preferably 99 mol % or more) in a very short period of time.

Moreover, it is particularly preferred, in the process according to the present invention, that the hydrogenation gas comprises an inerting gas that contributes to the pressure in the reactor with a partial pressure that corresponds to a contribution of up to 20%, preferably up to 5%, of the total pressure detected in the reactor. Nitrogen (which is preferred), rare gases or mixtures thereof can be used as inerting gas.

As can be seen in examples 1-17, the process developed by the inventors of the present application allows to obtain reactions at much lower pressures below 18 barg, preferably at least 7 barg, more preferably at least 8 barg, even more preferably at least 9 barg) with respect to the background art for several and numerous phthalic diesters, but especially for trimellitic triesters, using a broad range of catalysts.

A second aspect of the present invention relates to the use of hydrogenated 1,2,4-trimellitates, i.e., of trialkyl cyclohexane carboxylates obtainable/obtained for example by means of the above cited processes, in PVC as plasticizers in order to improve processing behavior with respect to the respective trimellitates. A further aspect of the present invention relates to new polymeric compositions characterized by an improved and expanded industrial applicability, comprising PVC and plasticizers constituted by 1,2,4-trialkyl cyclohexane carboxylates.

As is widely known, plasticizers are, generally speaking, organic compounds (mostly esters) that are added to certain polymers, predominantly but not necessarily thermoplastic ones, to improve their processing behavior and give them characteristics of flexibility and softness. The obtainment of these characteristics is due to the fact that generally, by subjecting mixtures of a polymer and a plasticizer to relatively high temperatures, an irreversible physical process occurs during which the molecules of plasticizer penetrate between the chains of the polymer. During this process, the chains of the polymer are mutually spaced, and in this manner there is a considerable reduction in intermolecular polymer-polymer attraction forces, which leads to greater mobility of the chains of said polymer. After cooling to ambient temperature, this effect can be detected macroscopically with a conspicuous reduction of the stiffness of the polymer. In addition to this main characteristic, some plasticizers can give the finished article other properties of considerable interest in application, such as for example elasticity, improved resistance to low temperatures, to atmospheric agents, etc.

The process in which the plasticizer molecules penetrate between the chains of the polymer is in practice decisive for processing behavior and can be studied by means of several physical phenomena, such as the dry blend time, the gelification time or fusion time, and the solution temperature according to the DIN 53408 method.

Plasticizers are compatible and therefore usable with a large number of polymers, in particular vinyl polymers, such as for example polyvinyl chloride (PVC) and polyvinyl acetate (PVA), cellulose polymers such as for example cellulose acetate (CA), acrylic resins, elastomers such as for example nitrile rubbers (NBR) and hydrogenated nitrile rubbers (HNBR), polyurethanes and others.

The technologies for the preparation of plasticized polymers require appropriate mixing of the polymer and the plasticizer. These mixtures are in two main physical forms: the dry blend, which is a powder in which the PVC has absorbed the plasticizer, and the paste or plastisol, which is a more or less viscous liquid constituted by a suspension of PVC in the plasticizer. The dry blend is generally processed in extruders, from which granules of plasticized polymer are produced which can be used in applications such as sheaths for electric cables, pipes, extensible films, etc. The plastisol is generally processed by spreading on several supports, in order to produce synthetic leathers, paving, wallpaper, insulating tapes, gaskets, etc. The fundamental technical problem of articles made of plasticized polymer is the permanence over time of the plasticizer in the conditions of use. Since the plasticizer is not bonded to the polymer by means of a chemical bond, it is in fact subject to release from the article, thus giving rise to a migration phenomenon. The extent of the migration is more or less great depending on parameters such as the molecular weight of the plasticizer, its volatility, temperature, irradiation, the presence of extracting solvents, etc. Plasticizers that, in the conditions of use, are characterized by a good degree of permanence, i.e., by a low migration rate, are usually considered plasticizers with good performance.

The plasticizers that by far are the most used are currently, as already noted, esters of phthalic acid, such as di-2-ethylhexyl phthalate (DEHP), di-isononyl phthalate (DINP) and di-isodecyl phthalate (DIDP). As a consequence of the concern linked to the toxicological properties of some phthalates, and with particular reference to the production of plasticized PVC articles intended for fields that are considered sensitive (medical articles, packaging for contact with food, toys and articles for children), in recent years plasticizer manufacturers have proposed commercially several alternative products, such as for example citrates, dibenzoates, terephthalates, acetylated glycerides, which however only rarely have a performance that can be compared to that of phthalates, and in most cases are characterized by a reduced degree of permanence.

Another path that has been followed has been to hydrogenate phthalates in order to yield the corresponding saturated products. The products obtained with the hydrogenation reaction are characterized by a molecular weight that is very similar to that of the corresponding phthalates, and therefore in general, from the point of view of permanence in the polymers, they do not differ greatly from the performance of phthalates. However, as already discussed above for di-isononyl cyclohexane 1,2 dicarboxylate (HDINP), in the application in PVC, hydrogenation compromises processing behavior, and the saturated product thus exhibits a reduced plasticizing efficiency, both with respect to the traditional plasticizer of reference (DEHP) and to its direct "homologue" (DINP).

As regards instead plasticizers constituted by trimellitates, it should be noted that they are substantially free from phthalates and therefore are not subject to the respective restrictions, and furthermore are characterized by an extremely low migration rate (which indeed qualifies them as plasticizers of the SP-LD class), and for these reasons it is believed that they entail, with respect to classic phthalates, a reduced risk of exposure for the end consumer. However, trimellitates are less workable with polymers, particularly PVC, than DEHP or DINP.

Surprisingly, during the study that led to the present invention, it was found that, differently from what is observed with 1,2 dialkyl cyclohexanecarboxylates, 1,2,4-trialkyl cyclohexane carboxylates instead have a better processing behavior in PVC and have a higher plasticizing efficiency than the corresponding aromatics (trimellitates).

In this study, saturated esters obtained by means of the hydrogenation process described in the present invention were subjected to an assessment as plasticizers of polyvinyl chloride (suspension PVC or S-PVC).

The characteristics that were assessed were the following:
absorption time at 83° C., 93° C. and 103° C. (dry blend time)
gelification time (or fusion time) at 88° C., 98° C., 108° C.
solution temperature according to DIN 53408
efficiency (Shore A hardness)
cold flexibility (Clash & Berg test)
mechanical characteristics
volatility
resistance to extraction in solvents (release in water, soapy water, olive oil, mineral oil)
compatibility in conditions of high humidity (tropical test)

The formulations used and the results of the tests are detailed in the examples.

The assessment, as PVC plasticizers, of 1,2,4-trialkyl cyclohexane carboxylates, preferably produced by means of the process described in the present invention, led to the following conclusions:

1) All 1,2,4-trialkyl cyclohexane carboxylates have better processing behavior in PVC than the corresponding aromatic "homologues", as pointed out by the reduction in gelification times, in dry blend times and the reduction in solution temperature.

The reduction of the gelification time, measured in the temperature range from 88° C. to 108° C. with 50 parts of plasticizer on 100 parts of S-PVC, amounts to at least 7%, preferably at least 15%, more preferably at least 30%, with respect to the use of the respective trimellitates or mixtures thereof. The above cited reductions in gelification time are detected preferably by means of torque measurements with a Brabender plastograph (W-50 cell). As described in the existing literature (e.g., Handbook of Plasticizers (2004), 205), the gelification time (or fusion time) is considered a measure of the compatibility of plasticizers (compatibility increases as the gelification time decreases).

The reduction of the dry blend time, measured in the temperature range from 83° C. to 103° C. with 50 or 60 parts of plasticizer on 100 parts of PVC, amounts to at least 5%, preferably 7%, with respect to the use of the respective trimellitates or mixtures thereof. Said reductions in dry blend time are detected preferably by means of torque measurements with a Brabender plastograph (P600 cell). Said temperature range (83° C.-103° C.) used in the tests is considered to be representative of actual production conditions, as described in the existing literature (e.g., Encyclopedia of PVC, second edition (1988), volume 2, 153).

The reduction of the solution temperature was determined by means of the DIN 53408 method.

2) All the 1,2,4-trialkyl cyclohexane carboxylates have a higher efficiency than the corresponding aromatic "homologues", as pointed out by the hardness reduction.

3) All the 1,2,4-trialkyl cyclohexane carboxylates have a volatility of the same order of magnitude, only slightly greater than the corresponding aromatic "homologues".

The volatility of a 1,2,4-trialkyl cyclohexane carboxylate with a relatively lower molecular weight (HTOTM) remains in any case 10 times lower than the volatility of dicarboxylic esters of general application (for example DEHP) and of replacement hydrogenated products introduced recently (di-isononyl cyclohexane 1,2 dicarboxylate).

4) All the 1,2,4-trialkyl cyclohexane carboxylates have a resistance to extraction in solvents and to humidity fully comparable to those of the corresponding aromatics.

5) The mechanical characteristics of the material plasticized with 1,2,4-trialkyl cyclohexane carboxylates are fully comparable to those of the material plasticized with the corresponding aromatics.

In conclusion, it has been found that the hydrogenation of aromatic polycarboxylic esters does not influence the performance of the molecules obtained as plasticizers of polymers in wide consumption, such as for example PVC in a predictable manner. For example, in the case of phthalates, the processing behavior of the hydrogenated esters is reduced with respect to that of the corresponding aromatic esters.

Surprisingly, the research conducted by the inventors of the present application points out that the hydrogenation of trimellitic esters allows instead to prepare plasticizers for PVC that are characterized not only by good compatibility but also by improved processing behavior (in comparison with "homologue" aromatic plasticizers) and good permanence in the PVC. Especially in mass production, the better processing behavior leads to an increased rate and therefore efficiency in production. In summary, the unexpected new characteristics of 1,2,4-trialkyl cyclohexane carboxylates expand the industrial usefulness, making their use interesting also outside the classic applications of the SP-LD type, traditionally reserved to their aromatic "homologues".

The present invention therefore provides, according to a further embodiment, new polymeric compositions comprising preferably PVC, more preferably S-PVC and a plasticizer selected from the group that consists of 1,2,4-trialkyl cyclohexane carboxylates, in which the non-cyclic monofunctional alkanol involved in the formation of the ester group is selected among alkanols comprising 1 to 16 carbon atoms or mixtures thereof. Preferably, this is a new polymeric composition comprising a polymer, preferably PVC or a mixture of PVC with another polymer, more preferably S-PVC or a mixture of S-PVC with another polymer, and at least one plasticizer selected from the group constituted by 1,2,4-tri-C1 cyclohexane carboxylate (HTM1), 1,2,4-tri-C2 cyclohexane carboxylate (HTM2), 1,2,4-tri-iC3 cyclohexane carboxylate (HTMI3), 1,2,4-tri-nC4 cyclohexane carboxylate (HTM4), 1,2,4-tri-nC4 cyclohexane carboxylate (HTMI4), 1,2,4-tri-2-ethylhexyl cyclohexane carboxylate (HTOTM), 1,2,4-tri-nC7-nC9 cyclohexane carboxylate (HTM7-9), 1,2,4-tri-nC8 cyclohexane carboxylate (HTM8), 1,2,4-tri-iC8 cyclohexane carboxylate (HTIOTM), 1,2,4-tri-nC8-nC10 cyclohexane carboxylate (HTM8-10), 1,2,4-tri-nC9 cyclohexane carboxylate (HTM9), 1,2,4-tri-nC9-nC11 cyclohexane carboxylate (HTM9-11), 1,2,4-tri-nC11 cyclohexane carboxylate (HTM11), 1,2,4-tri-nC9-iC9-nC11 cyclohexane carboxylate (HTM99-11), 1,2,4-tri-iC9 cyclohexane carboxylate (HTINTM) and 1,2,4-tri-nC12 cyclohexane carboxylate (HTM12). Preferably, the plasticizer is selected from the group consisting of 1,2,4-tri-2-ethylhexyl cyclohexane carboxylate (HTOTM), 1,2,4-tri-nC7-nC9 cyclohexane carboxylate (HTM7-9), 1,2,4-tri-nC8-nC10 cyclohexane carboxylate (HTM8-10), 1,2,4-tri-nC9-nC11 cyclohexane carboxylate (HTM9-11), 1,2,4-tri-nC9-iC9-nC11 cyclohexane carboxylate (HTM99-11) and 1,2,4-tri-iC9 cyclohexane carboxylate (HTINTM). The new polymeric compositions according to the invention can be used to obtain objects, including preferably insulators for electric cables, adhesive tapes, synthetic leathers for car interiors and other applications, extensible films, medical items, toys and others. The present invention therefore provides objects obtained from the new polymeric compositions described here.

The following examples are presented by way of illustration and are not intended to limit the protective scope defined by the claims.

EXAMPLES

Example 1

1200 g of TOTM at ambient temperature and pressure and 0.5% w, with respect to the substrate to be hydrogenated, of the commercial catalyst Chimet D4649 (5% by weight Pd/alumina) were loaded into a 2000-ml reactor.

After performing loading and inerting with nitrogen at ambient pressure, the T was increased to 150° C. before starting the reaction time by feeding hydrogen gas, with riser below an adapted agitator that facilitates the recycling of the hydrogen inside the reactor, after adjusting the P reduction unit on the hydrogen line to 15 barg and the initial flow-rate to 50 Nlt/h. The reaction is ended, interrupting the feeding of hydrogen, in a total of 5.5 hours, after verifying the absence of hydrogen consumption for 0.25-0.5 hours, after which the catalyst was separated appropriately from the product to be reused conveniently as is in a further synthesis, consequently reducing its specific consumption. The reactions thus performed lead to an average molar yield in 1,2,4-tri-2-ethylhexyl cyclohexane carboxylate (HTOTM) of 99.6% with an average conversion of 99.8% relative to the loaded TOTM.

Example 2

A synthesis of HTOTM as in example 1 was performed, but by loading 1.0% w on anhydrous base of commercial catalyst Engelhard 8016 (5% w of Rh on C), calculated on the loaded TOTM, with a hydrogen flow-rate of 33 Nlt/h. After a total of 6 hours of reaction, a molar yield in HTOTM of 99.9% was obtained, with a conversion of more than 99.9% relative to the loaded TOTM.

Example 3

A synthesis of HTOTM as in example 2 was performed, but by loading commercial catalyst Engelhard 9017 (5% w of Ru on C), and after 2.5 h, gradually increasing the reaction T to 170° C. 6 h after the beginning of the reaction, lack of consumption of hydrogen was observed; after a further hour, i.e., after a total of 7 h of operation, the reaction was stopped, obtaining a molar yield in HTOTM of 99.5%, with a 99.9% conversion relative to the loaded TOTM.

Example 4

180 g of TOTM, 1.0% w on anhydrous base of commercial catalyst Chimet U0706 (5% w of Ru on C), calculated on the loaded TOTM, were loaded into a 300-ml reactor and a synthesis as in example 1 was performed, but using an initial hydrogen flow-rate of 7.5 Nlt/h, and after 2 h the T was increased gradually to 170° C. The reaction was ended, interrupting the feeding of hydrogen, after a total of 5.5 hours, after keeping the temperature at 170° C. for 0.25-0.5 h without hydrogen consumption. The reaction thus performed had a molar yield in HTOTM of 99.4% with a 99.9% conversion relative to the loaded trimellitate.

Example 5

A synthesis of HTOTOM as in example 3 was performed, but by loading 1.0% w on anhydrous base, calculated on the loaded TOTM, of a 50/50p mixture of commercial catalysts Chimet D1175 and BASF 5011 RW ESCAT 111 (both 5% w of Pd on C), with a hydrogen flow-rate of 50 Nlt/h. After 2.5 h at 150° C., the temperature was increased gradually to 170° C. for 2 hours. After an hour without hydrogen consumption, i.e., after 5.5 hours of total operation, the reaction was stopped, obtaining a molar yield of HTOTM of 99.6% with a 99.8% conversion relative to the loaded TOTM.

Example 6

A synthesis as in example 1 was performed, but by loading 1,2,4-nC8nC10 trialkyl trimellitate (TM8-10) and 1.0% w of commercial catalyst Chimet D4649 (5% by weight of Pd/alumina), calculated on the loaded TM8-10. After a total of 4 h of operation, the reaction was stopped, obtaining a molar yield in 1,2,4-nC8nC10 trialkyl cyclohexane carboxylate (HTM8-10) of 99.3% with a 99.6% conversion relative to the loaded trimellitate.

Example 7

The catalyst used in example 6 was separated appropriately from the product to be reused conveniently as is in a subsequent synthesis, as in example 6, but by loading into the reactor 1,2,4-tri-n-octyl trimellitate (TM8). After a total of 4 h of operation, the reaction was stopped, obtaining a molar yield in 1,2,4-trioctyl cyclohexane carboxylate (HTM8) of 99.6% with a 99.9% conversion relative to the loaded trimellitate.

Example 8

180 g of 1,2,4-tri-nC7-nC9 trimellitate (TM7-9) were loaded into a 300-ml reactor and a synthesis was performed as in example 1, but by using an initial flow-rate of hydrogen of 7.5 Nlt/h and, after 4 h, gradually increasing the T to 160° C. The reaction was stopped after a total of 5.5 h, of which the last 0.25-0.5 h without hydrogen consumption, obtaining a molar yield in 1,2,4-tri-nC7-nC9 cyclohexane carboxylate (HTM7-9) of 99.6% with a 99.7 conversion relative to the loaded trimellitate.

Example 9

A synthesis as in example 1 was performed, but by loading 1,2,4-tri-n-butyl trimellitate (TM4), 1% of commercial catalyst Chimet D4649, calculated on the loaded TM4, using an initial flow-rate of 100 Nlt/h and gradually increasing the T to 160° C. after 2.5 h of operation; the reaction was ended after a total of 3.5 hours, of which the last 0.25-0.5 h without hydrogen consumption, obtaining a molar yield in 1,2,4-tributyl cyclohexane carboxylate (HTM4) of 99.8%, with a conversion of more than 99.9% relative to the loaded trimellitate.

Example 10

The catalyst used in example 9 was conveniently separated from the obtained product to be reused conveniently as is in a subsequent synthesis (as in example 9, but loading 1,2,4-tri-iC9 trimellitate (TINTM) and with a hydrogen flow-rate of 50 Nlt/h). The reaction was ended after a total of 4 h from the beginning of the reaction, obtaining a molar yield in 1,2,4-tri-iC9 cyclohexane carboxylate (HTINTM) of 99.3% with a 99.5% conversion relative to the loaded trimellitate.

Example 11

A synthesis was performed as an example 1, but by loading 1,2,4-tri-nC9 trimellitate (TM9) and gradually increasing the T to 160° C. after 2.5 h of operation; the reaction was stopped after a total of 4 h. The catalyst, conveniently separated from the product, was conveniently reused as is in 5 subsequent syntheses, reducing substantially its specific consumption and pointing out the possibility of being recycled further. The tests thus conducted led to an average molar yield in 1,2,4-tri-nC9 cyclohexane carboxylate (HTM9) of 99.7%, with an average conversion of 99.8% relative to the loaded trimellitate.

Example 12

A synthesis was performed as in example 11, but by loading 1,2,4-tri-nC9-nC11 trimellitate (TM9-11); the reaction was stopped after 4 h of total operation. The catalyst, conveniently separated from the product, was conveniently reused as is in 4 subsequent syntheses, reducing substantially its specific consumption and pointing out the possibility of being recycled further. The tests thus conducted led to an average molar yield in 1,2,4-tri-nC9-nC11 cyclohexane carboxylate (HTM9-11) of 99.8%, with an average conversion of more than 99.9% relative to the loaded trimellitate.

Example 13

A synthesis as in example 11 was performed, but by loading 1,2,4-tri-nC9-iC9-nC11 trimellitate (TM9-911) and gradually increasing the T to 170° C. after 1.5 h of operation; the reaction was ended after 4.5 h of total operation. The catalyst, conveniently separated from the product, was conveniently reused as is in 2 subsequent syntheses, reducing substantially its specific consumption and pointing out the possibility of being recycled further. The tests thus conducted led to an average molar yield in 1,2,4-tri-nC9-iC9-nC11 cyclohexane carboxylate (HTM9-911) of 99.4%, with an average conversion of 99.5% relative to the loaded trimellitate.

Example 14

A synthesis as in example 9 was performed, but by loading 1,2,4-trimethyl trimellitate (TM1); the reaction was ended after a total of 5 h from the beginning of the reaction. The catalyst, conveniently separated from the product, was conveniently reused as is in 2 subsequent syntheses, reducing significantly its specific consumption and pointing out the possibility of recycling it further. The tests thus conducted led to an average molar yield in 1,2,4-trimethyl cyclohexane carboxylate (HTML) of 99.5%, with an average conversion of 99.6% relative to the loaded trimellitate.

Example 15

A series of hydrogenations as in example 1 was performed, but by loading DEHP and increasing the T to 160° in the last 0.5-1.0 h of reaction, and ending the feeding of hydrogen after 0.25-0.5 h without hydrogen consumption. The catalyst, conveniently separated from the product, was conveniently reused as is in 12 subsequent syntheses, reducing substantially its specific consumption and pointing out the possibility of recycling it further.

The tests thus conducted led to an average conversion of 99.93% in 4.5-5 h of total operation with an average molar yield in di-2-ethylhexyl cyclohexane carboxylate (HDEHP) of 99.91% relative to the loaded DEHP.

Example 16-17

2 series of hydrogenations as in example 15 were performed, but by loading in the reactor respectively di-isononyl phthalate (DINP) and dialkyl phthalates of mixtures of C9-C11 alkanols (DIPLAST L9-11"). The catalyst, conveniently separated from the product, was conveniently reused in subsequent syntheses, reducing significantly its specific consumption and pointing out the possibility to recycle it further, beyond the number of recyclings performed in these examples.

The conversions, yields, recyclings and total reaction times obtained are listed in the following table.

| Example (no.) | Aromatic | T (h) total run | Cat. recyclings (no.) | Conversion | Yield in 1,2 dialkyl cyclohexane carboxylate (% molar) |
|---|---|---|---|---|---|
| 16 | DINP | 4.5 | ≥10 | >99.9 | 99.8 |
| 17 | L9-11 | 6 | ≥10 | 99.7 | 99.5 |

Example 18

The following compositions (expressed in parts by weight) of plasticizers with suspension grade PVC (S-PVC) were prepared:

| Formulation 1 | |
|---|---|
| PVC K70 | 100 |
| Plasticizer | 50 |
| Ba/Zn Stabilizer | 1.2 |
| Stearic acid | 0.3 |

| Formulation 2 | |
|---|---|
| PVC K70 | 100 |
| Plasticizer | 60 |
| Ba/Zn Stabilizer | 1.2 |
| Stearic acid | 0.3 |

Using the above cited compositions, a targeted rheological assessment thereof was performed with the aim of establishing a scale of compatibility and processing behavior of the plasticizers being considered. In particular, the following tests were conducted:

absorption time at 83° C., 93° C. and 103° C. (dry blend time), by means of torque measurements with a Brabender plastograph (P600 cell).

gelification time (or fusion time) at 88° C., 98° C., 108° C., by means of torque measurements with a Brabender plastograph (W-50 cell).

The results of these tests are given in the following tables:

| Test | DEHP | DINP | HDINP |
|---|---|---|---|
| Dry Blend time 83° C.* | 2'46" | 3'14" | 4'02" |
| Dry Blend time 93° C.* | 1'30" | 1'46" | 2'24" |
| Dry Blend time 103° C.** | 1'24" | 1'28" | 2'08" |
| Fusion time 88° C.* | 5'14" | 7'44" | 34'06" |
| Fusion time 98° C.* | 4'10" | 5'30" | 18'26" |
| Fusion time 108° C.* | 2'44" | 3'28" | 9'36" |

*Formulation 1
**Formulation 2

| Test | TM4 | HTM4 | TOTM | HTOTM | TM8 | HTM8 | TINTM | HTINTM | TM8-10 | HTM8-10 | TM99-11 | HTM99-11 |
|---|---|---|---|---|---|---|---|---|---|---|---|---|
| Dry Blend time 83° C.* | 1'34" | 1'16" | 4'48" | 4'08" | 4'20" | 3'52" | 6'12" | 5'18" | 6'42" | 5'24" | 9'32" | 7'46" |
| Dry Blend time 93° C.* | 1'00" | 42" | 2'46" | 2'34" | 2'44" | 2'20" | 3'38" | 2'36" | 4'08" | 2'58" | 5'10" | 4'28" |
| Dry Blend time 103° C.** | NV(1) | NV(1) | 2'22" | 2'10" | 2'32" | 2'00" | 3'32" | 2'28" | 3'36" | 2'44" | 4'46" | 4'18" |
| Fusion time 88° C.* | 2'35" | 2'08" | 9'54" | 6'50" | 18'56" | 8'26" | 29'24" | 17'40" | 51'50" | 17'02" | NV(2) | 41'16" |
| Fusion time 98° C.* | 1'42" | 1'24" | 6'04" | 4'06" | 9'18" | 6'28" | 20'10" | 10'24" | 35'38" | 11'20" | NV(2) | 23'16" |

-continued

| Test | TM4 | HTM4 | TOTM | HTOTM | TM8 | HTM8 | TINTM | HTINTM | TM8-10 | HTM8-10 | TM99-11 | HTM99-11 |
|---|---|---|---|---|---|---|---|---|---|---|---|---|
| Fusion time 108° C.* | 1'19" | 1'06" | 3'46" | 2'36" | 6'04" | 3'12" | 10'30" | 5'44" | 17'20" | 7'14" | 41'30" | 16'38" |

*Formulation 1
**Formulation 2
NV(1) = Not assessable (at this temperature the gelification process occurs and this makes it impossible to determine the dry blend process)
NV(2) = Not assessable (after 60 minutes, the gelification process had not begun)

Using only formulation 1, the following tests were further performed:
- efficiency (Shore A hardness)
- cold flexibility (Clash & Berg test)
- mechanical characteristics
- volatility
- resistance to extraction in solvents (release in water, soapy water, olive oil, mineral oil)
- compatibility in conditions of high humidity (tropical test)

the results of which are shown in the following table:

| Assessment in S-PVC* | | | | | | | | |
|---|---|---|---|---|---|---|---|---|
| | DEHP | HDINP | TOTM | HTOTM | TINTM | HTINTM | TM8-10 | HTM8-10 |
| Shore A hardness 15 seconds (ISO 868) | 80 | 86 | 89 | 86.5 | 90.5 | 88.5 | 91 | 89 |
| Clash & Berg ° C. (ISO/R 458) | −25 | −29 | −16.5 | −14 | −24 | −18 | −31.5 | −28 |
| Volatility-mass loss % 7 days at 100° C. (ISO 176) | −12.3 | −10.6 | −0.5 | −0.88 | −0.43 | −0.53 | −0.57 | −0.69 |
| Releases (after 48 hours at 70° C.) 1 mm (ISO 175) | | | | | | | | |
| 100% demineralized H2O | | | | | | | | |
| Weight loss % | — | — | −0.06 | −0.12 | −0.09 | −0.09 | −0.1 | −0.1 |
| 1% soapy H2O | | | | | | | | |
| Weight loss % | — | — | +0.08 | −0.17 | +0.11 | +0.11 | +0.12 | +0.08 |
| Olive oil | | | | | | | | |
| Weight loss % | — | — | −2.87 | −3.14 | −8.68 | −6.69 | −14.14 | −11.49 |
| Mineral oil | | | | | | | | |
| Weight loss % | — | — | −2.32 | −2.57 | −3.13 | −3.12 | −6.28 | −5.43 |
| 80° C. tropical test | | | | | | | | |
| After 4 weeks** | — | — | Dry | Dry | Dry | Dry | Dry | Dry |

*Formulation 1
(**Dry = no exudation after 4 weeks at 80° C. in 100% humidity conditions)

The above cited composition was used to perform the following tests:
- absorption time at 83° C. (dry blend time), by means of torque measurements with a Brabender plastograph (P600 cell).
- efficiency (Shore D hardness)
- cold flexibility (Clash & Berg test)
- mechanical characteristics

Example 19

The following composition (expressed in parts by weight) was prepared and can be considered suitable for the production of insulators for electrical cables:

| | |
|---|---|
| S-PVC K70 | 100 |
| PLASTICIZER* | 47 |
| Stabilizing Ca/Zn | 8 |
| CaCO3 | 15 |
| Ca stearate type E | 0.5 |

*containing furthermore 0.3% by weight of antioxidant pentaerythritol tetrakis(3-(3,5-di-tert-butyl-4-hydroxyphenyl)propionate) (CAS number 6683-19-8).

| | TOTM | HTOTM | TINTM | HTINTM | TM 8-10 | HTM 8-10 |
|---|---|---|---|---|---|---|
| Dry Blend time 83° C. | 3'32" | 3'14" | 4'32" | 4'02" | 4'44" | 4'04" |
| Shore D hardness 15 seconds | 44 | 42.5 | 47 | 44.5 | 45.5 | 42.5 |
| Clash & Berg ° C. (ISO/R 458) | −13 | −9.5 | −17 | −14 | −24 | −21 |
| Mechanical characteristics (1 mm thickness) | | | | | | |
| Tensile strength MPa | 22.9 | 22.6 | 21.8 | 21.7 | 21.2 | 20.5 |
| Breaking elongation % | 287 | 280 | 284 | 280 | 291 | 275 |

-continued

|  | TOTM | HTOTM | TINTM | HTINTM | TM 8-10 | HTM 8-10 |
|---|---|---|---|---|---|---|
| 100% modulus MPa | 14.9 | 14.5 | 14.4 | 14.2 | 13.4 | 13.2 |

Example 20

The solution temperature test (according to DIN 53408) was performed and its results are shown in the following table:

Solution temperature (according to DIN 53408)

|  | DEHP | DINP | HDINP | TOTM | HTOTM | TM8 | HTM8 | TINTM | HTINTM | TM8-10 | HTM8-10 | TM9-911 | HTM9-911 |
|---|---|---|---|---|---|---|---|---|---|---|---|---|---|
| Detected T ° C. | 120 | 128 | 149 | 140 | 137 | 145 | 137 | 148 | 146 | 154 | 151 | 159 | 156 |

The disclosures in Italian Patent Application No. MI2012A001641 from which this application claims priority are incorporated herein by reference.

The invention claimed is:

1. A process for the semi-continuous catalytic liquid phase hydrogenation of esters of aromatic carboxylic diacids and triacids, wherein the esters, loaded in a reactor without adding diluent/solvent, are hydrogenated at an internal temperature of the reactor comprised in the range from 100° C. to 200° C., by continuously feeding a hydrogenation gas into the reactor, controlling the hydrogenation gas pressure inside the reactor to values in the range from at least 7 bar gauge (barg) to below 18 barg and in the presence of 0.1-3% by weight relative to the quantity of esters of aromatic carboxylic acids loaded into the reactor, of a supported catalyst comprising between 0.1 and 10% by weight, relative to the total weight of the catalyst, of an active metal of the group consisting of ruthenium, rhodium, palladium, osmium, iridium, platinum, gold or mixtures thereof, and optionally of at least one additional metal selected from groups I-III of the periodic system, also present at most as 10% by weight, relative to the total quantity of catalyst, and present in a quantity that does not exceed that of the active metal.

2. The process according to claim 1 for the semi-continuous catalytic liquid phase hydrogenation of esters of aromatic carboxylic diacids and triacids, selected from diesters of phthalic acid and triesters of 1,2,4-benzene tricarboxylic acid, wherein the esters, loaded in a reactor without adding diluent/solvent, are hydrogenated at an internal temperature of the reactor comprised in the range from 130° C. to 170° C., by continuously feeding a hydrogenation gas into the reactor, controlling the hydrogenation gas pressure inside the reactor to values in the range from at least 7 barg to below 18 barg and in the presence of 0.3-1.5% by weight, relative to the quantity of esters of aromatic carboxylic acids loaded into the reactor, of a supported catalyst comprising between 0.1 and 10% by weight, relative to the total weight of the catalyst, of an active metal of the group consisting of ruthenium, rhodium, palladium, osmium, iridium, platinum, gold or mixtures thereof, and optionally of at least one additional metal selected from groups I-III of the periodic system, also present at most as 10% by weight, relative to the total quantity of catalyst, and present in a quantity that does not exceed that of the active metal.

3. The process according to claim 1, wherein aromatic carboxylic diacid esters are used which are selected from phthalic acid diesters with non-cyclic monofunctional alkanols comprising 1 to 16 carbon atoms or mixtures thereof.

4. The process according to claim 1, wherein aromatic carboxylic triacid esters are used which are selected from triesters of 1,2,4-benzene tricarboxylic acid with non-cyclic monofunctional alkanols comprising 1 to 16 carbon atoms or mixtures thereof.

5. The process according to claim 4, wherein the non-cyclic monofunctional alkanol is selected from the group consisting of methanol, ethanol, n-butanol, sec-butanol, iso-butanol, tert-butanol, n-hexanol, 2-ethyl hexanol, n-heptanol, n-octanol, n-nonanol, i-nonanol, n-decanol, i-decanol, n-undecanol, n-dodecanol or mixtures thereof.

6. The process according to claim 4, wherein the non-cyclic monofunctional alkanol comprises 7-12 carbon atoms.

7. The process according to claim 1, wherein the catalyst comprises an active metal selected from Ru, Rh or Pd or mixtures thereof on a coal or alumina support.

8. The process according to claim 7, wherein the catalyst is selected from Pd on alumina, Pd on coal, Ru on coal or Rh on coal or mixtures thereof.

9. The process according to claim 1, wherein the hydrogenation gas comprises an inerting gas which contributes to the pressure in the reactor with a partial pressure that corresponds to a contribution of up to 20% of the total pressure detected in the reactor.

10. The process according to claim 6, wherein the feeding of hydrogenation gas is controlled during the hydrogenation reaction so as to increase the pressure inside the reactor with increasing conversion, and wherein the feeding of hydrogenation gas is interrupted when the internal pressure of the reactor reaches a value comprised in the range from 9 to 15 barg at an internal temperature comprised in the range from 150° C. to 170° C., without consumption of hydrogen for about 0.25-1.0 hours, after which the reaction mix is subjected to the separation of the hydrogenated esters that have formed.

11. The process according to claim 1, wherein the esters of aromatic carboxylic diacids and triacids are selected from diesters of phthalic acid and triesters of 1,2,4-benzene tricarboxylic acid.

12. The process according to claim 1, wherein the esters are hydrogenated at an internal temperature of the reactor comprised in the range from 120° C. to 190° C.

13. The process according to claim 1, wherein the esters are hydrogenated at an internal temperature of the reactor comprised in the range from 130° C. to 180° C.

14. The process according to claim 1, wherein the esters are hydrogenated at an internal temperature of the reactor comprised in the range from 140° C. to 170° C.

15. The process according to claim 1, wherein the hydrogenation gas pressure inside the reactor is equal to or lower than 15 barg.

16. The process according to claim 1, wherein the hydrogenation gas pressure inside the reactor is comprised in the range from 9 to 15 barg.

17. The process according to claim 1, wherein the supported catalyst is present in an amount from 0.3 to 1.5% by weight, relative to the quantity of esters of aromatic carboxylic acids loaded into the reactor.

18. The process according to claim 2, wherein the hydrogenation gas pressure inside the reactor is comprised in the range from 9 to 15 barg.

19. The process according to claim 5, wherein the non-cyclic monofunctional alkanol is selected from the group consisting of 2-ethyl hexanol, n-heptanol, n-octanol, n-nonanol, i-nonanol, n-decanol, i-decanol, n-undecanol, n-dodecanol- or mixtures thereof.

20. The process according to claim 5, wherein the non-cyclic monofunctional alkanol is 2-ethyl hexanol.

21. The process according to claim 6, wherein the non-cyclic monofunctional alkanol comprises 8-11 carbon atoms.

22. The process according to claim 6, wherein the non-cyclic monofunctional alkanol comprises 8-10 carbon atoms.

23. The process according to claim 8, wherein the active metal is present between 1.5 and 7.0% by weight, relative to the total weight of the catalyst.

* * * * *